United States Patent
Xu

(10) Patent No.: US 9,624,185 B1
(45) Date of Patent: Apr. 18, 2017

(54) METHOD FOR PREPARING IDO INHIBITOR EPACADOSTAT

(71) Applicant: Yong Xu, San Diego, CA (US)

(72) Inventor: Yong Xu, San Diego, CA (US)

( * ) Notice: Subject to any disclaimer, the term of this patent is extended or adjusted under 35 U.S.C. 154(b) by 0 days.

(21) Appl. No.: 15/001,484

(22) Filed: Jan. 20, 2016

(51) Int. Cl.
*C07D 271/08* (2006.01)

(52) U.S. Cl.
CPC .................. *C07D 271/08* (2013.01)

(58) Field of Classification Search
CPC .................................................... C07D 271/08
See application file for complete search history.

(56) References Cited

U.S. PATENT DOCUMENTS

| | | | |
|---|---|---|---|
| 2010/0015178 A1* | 1/2010 | Combs | C07D 271/08 424/204.1 |
| 2012/0058079 A1* | 3/2012 | Combs | C07D 271/08 424/85.2 |
| 2014/0023663 A1* | 1/2014 | Combs | C07D 271/08 424/173.1 |
| 2015/0133674 A1* | 5/2015 | Tao | C07C 307/06 548/132 |
| 2015/0190378 A1* | 7/2015 | Combs | C07D 271/08 514/364 |
| 2015/0352206 A1* | 12/2015 | Gajewski | A61K 31/4245 424/142.1 |

* cited by examiner

*Primary Examiner* — Valerie Rodriguez-Garcia
(74) *Attorney, Agent, or Firm* — Kile Park Reed & Houtteman PLLC

(57) ABSTRACT

The present disclosure provides a new method for preparing IDO inhibitor epacadostat. The whole reaction route is simple, easy to control and has high yield.

19 Claims, No Drawings

METHOD FOR PREPARING IDO INHIBITOR EPACADOSTAT

FIELD

The present disclosure relates to a chemical medicine field, it relates generally to the synthesis of IDO inhibitor epacadostat. Specifically, the disclosure relates to the process for preparation of epacadostat and intermediates thereof.

BACKGROUND

Epacadostat is a selective inhibitor of the enzyme IDO (indoleamine 2, 3-dioxygenase enzyme) which is an immunosuppressive molecule expressed in cancer and dendritic cells, and selectively knocks down the expression of the gene of the enzyme IDO. It is an immune-based cancer therapy using gene silence of epacadostat in dendritic cells. Epacadostat is used for the treatment of cancers, solid tumors such as metastatic melanoma, ovarian cancer and non-small cell lung cancer. Epacadostat has the structural formula shown as Formula 1:

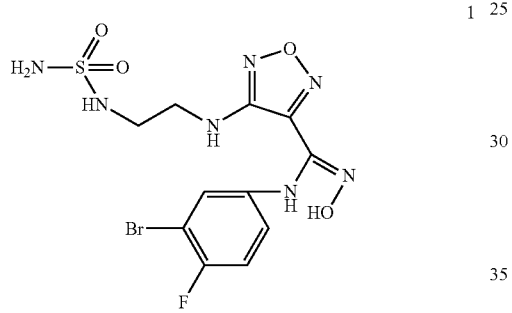

1

International patent application Publication No. WO2010/005958 disclose 1,2,5-oxadiazoles as inhibitors of indoleamine 2,3-dioxygenase and the preparation method thereof. Malononitrile, sodium nitrite and hydroxylamine hydrochloride are used as starting materials for preparation of epacadostat; and the total synthesis of epacadostat was achieved in over 10 steps. Therefore, the current synthesis method of epacadostat is still to be improved.

SUMMARY

It is an object of the present disclosure to provide a method for preparing IDO inhibitor epacadostat to improve the process for the synthesis of epacadostat, thereby avoiding at least one of the disadvantages described above.

One aspect of the present disclosure, according to an embodiment of the present disclosure, provides a method for preparing epacadostat. According to some embodiments of the present embodiments, the method for preparing epacadostat includes the steps of: (1) contacting a compound of formula 2 with sodium nitrite and hydroxylamine hydrochloride to obtain a compound of formula 3; (2) contacting the compound of formula 3 with a compound of formula 4 to obtain a compound of formula 5; (3) contacting the compound of formula 5 with N,N'-carbonyldiimidazole to obtain a compound of formula 6; (4) contacting the compound of formula 6 with ethyleneimine to obtain a compound of formula 7; (5) contacting the compound of formula 7 with a compound of formula 8 to obtain a compound of formula 9; and (6) contacting the compound of formula 9 with sodium hydroxide to obtain the epacadostat of formula 1;

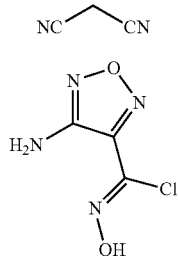

2

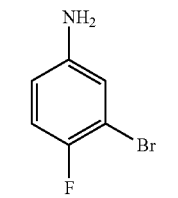

3

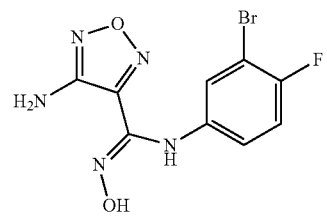

4

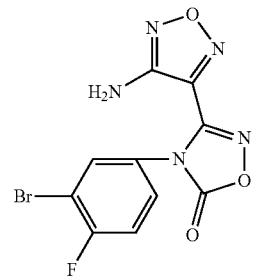

5

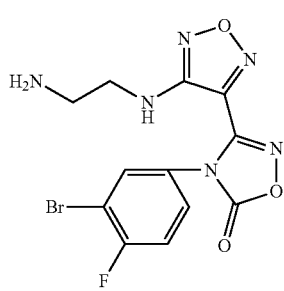

6

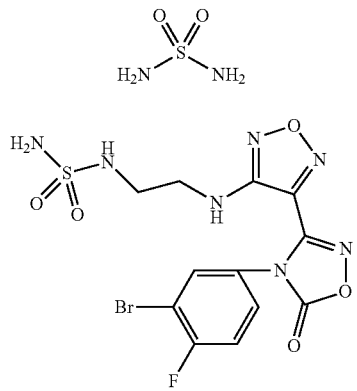

7

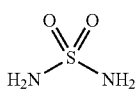

8

9

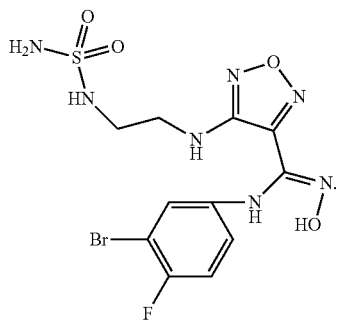

It has now been found, surprisingly, in the present invention, through adopting the ethyleneimine as reactant, the process is shortened surprisingly, and the application of this route is applied to reduce the reaction conditions and improve the yield of the product. And the whole reaction route is simple, economic and easy to control, has high yield, and does not use harsh conditions such as high temperature and high pressure.

According to some embodiments of the present embodiments, the step (1) comprises the steps of: (1-1) dissolving the compound of formula 2 and sodium nitrite in water under about 10° C., adding concentrated hydrochloric acid into the resulting mixture under a temperature below 15° C. to obtain a first mixture, and stirring the first mixture at room temperature for about 1 hour to about 3 hours; (1-2) adding hydroxylamine hydrochloride into the first mixture to obtain a second mixture, and stirring the second mixture for about 1 hour; (1-3) heating the second mixture at refluxing temperature for about 1 hour to about 3 hours, then cooling down the temperature of the second mixture to room temperature, then adjusting pH of the second mixture to about 7 by adding NaOH solution; (1-4) centrifugating the resulting reaction product of the step (1-3) to obtain a first precipitation; (1-5) dissolving the first precipitation in a mixture of water, acetic acid and hydrochloric acid by heating, and adding sodium nitrite aqueous solution into the resulting mixture under a temperature ranging from about −10° C. to about 10° C. to obtain a third mixture, and stirring the third mixture for about 1 hour to about 3 hours at room temperature to obtain a second precipitation; (1-6) dissolving the second precipitation in ethyl acetate to obtain a fourth mixture; (1-7) obtaining an oily substance by drying and concentrating the organic phase of the fourth mixture; (1-8) dissolving the oily substance in methyl tertiary butyl ether to obtain a fifth mixture, and discoloring the fifth mixture with active carbon; (1-9) concentrating the resulting reaction product of the step (1-8) to obtain the compound of formula 3.

According to some embodiments of the present embodiments, a molar ratio between the compound of formula 2, sodium nitrite and hydroxylamine hydrochloride is 1: (1.95-2.1): (2.8-3.1), so as to improve the synthetic yield of the compound of formula 3.

According to some embodiments of the present embodiments, the molar ratio between the compound of formula 2, sodium nitrite and hydroxylamine hydrochloride is 1:1.99:3, so as to improve the synthetic yield of the compound of formula 3.

According to some embodiments of the present embodiments, the compound of formula 3 is contacted with the compound of formula 4 in ethanol under a condition of refluxing.

According to some embodiments of the present embodiments, the amount of the compound of formula 4 is 2 equivalents to 3.5 equivalents per 1 equivalent by mole of the compound of formula 3, so as to improve the synthetic yield of the compound of formula 5.

According to some embodiments of the present embodiments, the amount of the compound of formula 4 is 2.99 equivalents per 1 equivalent by mole of the compound of formula 3, so as to improve the synthetic yield of the compound of formula 5.

According to some embodiments of the present embodiments, the compound of formula 5 is contacted with N,N'-carbonyldiimidazole in ethyl acetate under a temperature ranging from about 60° C. to about 70° C. for about 1 hour to about 3 hours, when the temperature goes beyond the range of about 60° C. to about 70° C., the synthetic efficiency of the compound of formula 6 may be reduced significantly. When the temperature is lower than about 60° C., the synthetic efficiency of the compound of formula 6 may be reduced significantly. And the inventor surprisingly found that when the temperature exceeds about 70° C., the synthetic efficiency of the compound of formula 6 will also be reduced significantly, perhaps because the temperature may influence the reaction of the step (3).

According to some embodiments of the present embodiments, the amount of N,N'-carbonyldiimidazole is 1 equivalent to 1.5 equivalents per 1 equivalent by mole of the compound of formula 5, so as to improve the synthetic yield of the compound of formula 6.

According to some embodiments of the present embodiments, the amount of N,N'-carbonyldiimidazole is 1.11 equivalent to per 1 equivalent by mole of the compound of formula 5, so as to improve the synthetic yield of the compound of formula 6.

According to some embodiments of the present embodiments, the compound 6 is contacted with ethyleneimine in acetone under a temperature ranging from about −10° C. to about 5° C. for about 1 hour to 4 hours, when the temperature goes beyond the range of about −10° C. to about 5° C., the synthetic efficiency of the compound of formula 7 may be reduced significantly. When the temperature is lower than about −10° C., the synthetic efficiency of the compound of formula 7 may be reduced significantly. And the inventor surprisingly found that when the temperature exceeds about 5° C., the synthetic efficiency of the compound of formula 7 will also be reduced significantly, perhaps because the temperature may influence the reaction of the step (4).

According to some embodiments of the present embodiments, the amount of ethyleneimine is 1 equivalent to 1.3 equivalents per 1 equivalent by mole of the compound of formula 6, so as to improve the synthetic yield of the compound of formula 7.

According to some embodiments of the present embodiments, the amount of ethyleneimine is 1.05 equivalents per 1 equivalent by mole of the compound of formula 6, so as to improve the synthetic yield of the compound of formula 7.

According to some embodiments of the present embodiments, the step (5) comprises the steps of: (5-1) contacting the compound of formula 7 with the compound of formula 8 in triethylamine under a temperature ranging from about 120° C. to about 140° C. with microwave radiation for about 15 minutes to about 1 hour to obtain a sixth mixture; (5-2) cooling down the temperature of the sixth mixture to room temperature, and adding ethyl acetate into the sixth mixture to obtain an seventh mixture; (5-3) washing the organic phase of the seventh mixture with aqueous HCl solution, dehydrating the organic phase of the seventh mixture with anhydrous sodium sulfate, then concentrating the organic phase of the seventh resulting mixture to obtain the compound of formula 9.

According to some embodiments of the present embodiments, the amount of the compound of formula 8 is 1.05 equivalents to 1.5 equivalents per 1 equivalent by mole of the compound of formula 7, so as to improve the synthetic yield of the compound of formula 9.

According to some embodiments of the present embodiments, the amount of the compound of formula 8 is 1.2 equivalents per 1 equivalent by mole of the compound of formula 7, so as to improve the synthetic yield of the compound of formula 9.

According to some embodiments of the present embodiments, the step (6) comprise the steps of: (6-1) dissolving the compound 9 in THF under a temperature ranging from about −10° C. to about 5° C.; (6-2) adding sodium hydroxide solution into the solution obtained by the step (6-1) at room temperature to obtain an eighth mixture, and stirring the eighth mixture for 2 hours; (6-3) adjusting the pH of the eighth mixture of the step (6-2) to about 3 to about 4 by adding hydrochloric acid solution, and adding ethyl acetate in to the eighth mixture to obtain a ninth resulting mixture; (6-4) washing the ninth mixture with water and saturated sodium chloride solution respectively, and concentrating the ninth mixture to obtain epacadostat of formula 1.

According to some embodiments of the present embodiments, the amount of sodium hydroxide is 3.25 equivalents to 4.18 equivalents per 1 equivalent by mole of the compound of formula 9, so as to improve the synthetic yield of the epacadostat of formula 1.

According to some embodiments of the present embodiments, the amount of sodium hydroxide is 3.71 equivalents per 1 equivalent by mole of the compound of formula 9, so as to improve the synthetic yield of the epacadostat of formula 1.

DETAILED DESCRIPTION

The term "contacting" herein should be understood broadly, allowing any of at least two reactants react; for example, two reactants to be mixed under appropriate condition. According to the experimental requirements, mixing the reactants with which need to be contacted under stirring. Therefore, the type of agitation is not particularly limited. For example, may be a mechanical agitation, i.e. under the action of mechanical forces stirring.

As used herein, "a compound of formula N" is sometimes also referred to "Compound N". For example, "a compound of formula 2" may also be referred to "compound 2".

In this article, the term "first" or "second" is only used for describing objective other than indicate or imply relative importance or implicit indicate the number of technical features or technical solutions. Thus, defining the "first", the "second" features may explicitly or implicitly includes one or more of the characteristics. In the description of the disclosure, "multiple" means two or more, unless otherwise specifically limited.

According to the present disclosure, it is devised a process of preparing a compound of formula 1:

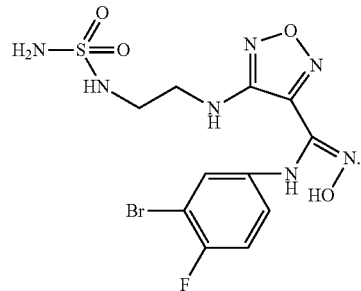

The technical solutions of the present disclosure include: the compound of formula 3 is prepared by a process comprising reacting the compound of formula 2 (malononitrile) with sodium nitrite and hydroxylamine hydrochloride, the compound of formula 5 is prepared by a process comprising reacting the compound of formula 3 with the compound of formula 4, the compound of formula 6 is prepared by a process comprising reacting the compound of formula 5 with N,N'-carbonyldiimidazole, the compound of formula 7 is prepared by a process comprising reacting the compound of formula 6 with ethyleneimine, the compound of formula 9 is prepared by a process comprising reacting the compound of formula 7 with the compound of formula 8, the compound of formula 1 (epacadostat) is prepared by a process comprising reacting the compound of formula 9 with sodium hydroxide.

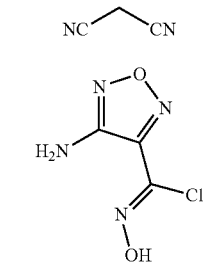

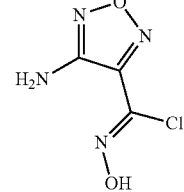

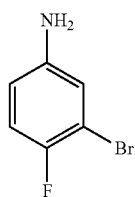

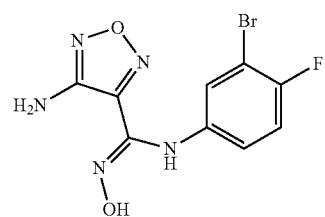

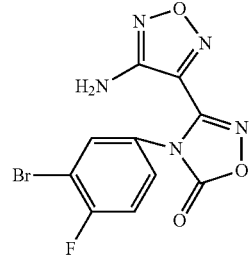

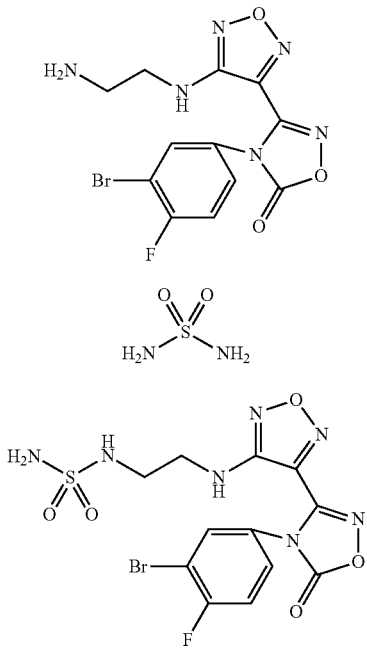

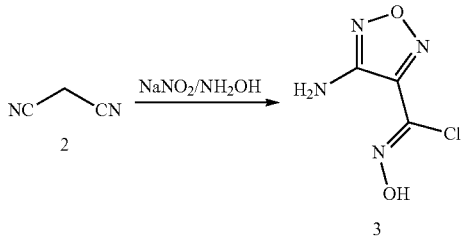 [SMILES: N#CCC#N ; Nc1nonc1/C(Cl)=N/O]

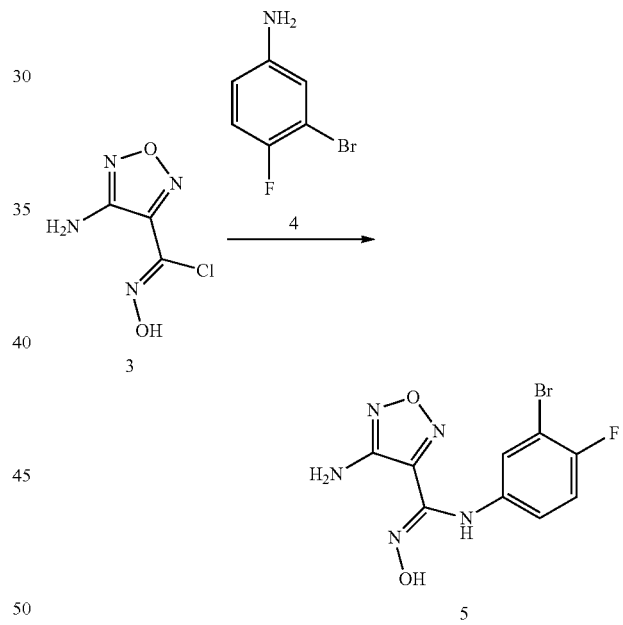

According to some embodiments of the present disclosure, a method for preparing epacadostat of formula 1 includes the following steps:

Step (1): the compound of formula 2 is contacted with sodium nitrite and hydroxylamine hydrochloride to give the compound of formula 3.

Step (2): the compound of formula 3 is contacted with the compound of formula 4 to give the compound of formula 5.

Step (3): the compound of formula 5 is contacted with N,N'-carbonyldiimidazole to give the compound of formula 6.

Step (4): the compound of formula 6 is contacted with ethyleneimine to give the compound of formula 7.

Step (5): the compound of formula 7 is contacted with the compound of formula 8 to give the compound of formula 9.

Step (6): the compound of formula 9 is contacted with sodium hydroxide to give the epacadostat of formula 1.

In some embodiments, in the method disclosed herein, the preparation method of the present invention is as follows.

According to some embodiments of the present disclosure, in the step (1) of the method, the compound of formula 2, sodium nitrite and water are added into the first reactor, then the first reactor is cooled under 10° C., concentrated hydrochloric acid is added and the temperature was kept below 15° C., then the mixture was kept at room temperature, stirred for 1 hour to 3 hours. Then hydroxylamine hydrochloride is added, and the mixture is stirred for 1 hour. The the mixture is heated to reflux for 1 hour to 3 hours, cooled to room temperature, add NaOH solution to adjust the pH to 7. The reactor is cooled and then centrifugated to obtain solid precipitation. The wet solid precipitation is dissolved in water, acetic acid and hydrochloric acid by heating. Sodium nitrite aqueous solution is added and the reactor is kept at −10° C.~10° C., and the mixture is stirred for 1 hour to 3 hours, and then the mixture is kept at room temperature. The precipitated reaction product is filtered and dissolved in ethyl acetate. The organic phase is washed by saturated sodium chloride aqueous solution, then dried and concentrated to obtain oily substance. The oily substance is dissolved in methyl tertiary butyl ether, discolored with active carbon. The solution is filtered and concentrated to give the compound of formula 3.

According to some embodiments of the present disclosure, a molar ratio between the compound of formula 2, sodium nitrite and hydroxylamine hydrochloride is 1:(1.95-2.1):(2.8-3.1) in the step (1). In other embodiments, the molar ratio between the compound of formula 2, sodium nitrite and hydroxylamine hydrochloride is 1:1.99:3 in the step (1).

According to some embodiments of the present disclosure, the compound of formula 3, the compound of formula 4 and ethanol are added into the second reactor, then the reactor is heated to reflux for 30 minutes to 2 hours, then the mixture is concentrated, and the crude product is washed with n-hexane/ethyl acetate, filtered, dried to obtain the compound of formula 5.

According to some embodiments of the present disclosure, in the method disclosed herein, the compound of formula 4 in step (2) may be used at an amount of 2.0 equivalents to 3.5 equivalents per 1 equivalent by mole of the compound of formula 3. In other embodiments, the compound of formula 4 in step (2) may be used at the amount of 2.99 equivalents per 1 equivalent by mole of the compound of formula 3.

According to some embodiments of the present disclosure, in the step (3) of the method, the compound of formula 5 and ethyl acetate are added into the third reactor, then added N,N'-carbonyldiimidazole into the third reactor at room temperature. The reactor is heated to 60° C.-70° C., then stirred for 1 hour to 3 hours, cooled down to room temperature, the mixture is concentrated, the solid residue is washed with n-hexane to obtain the compound of formula 6.

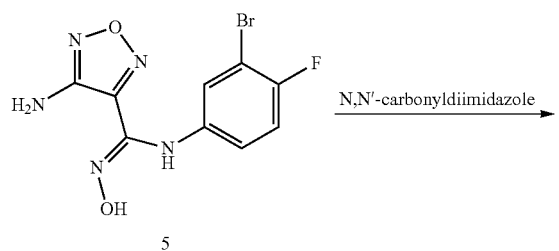

5

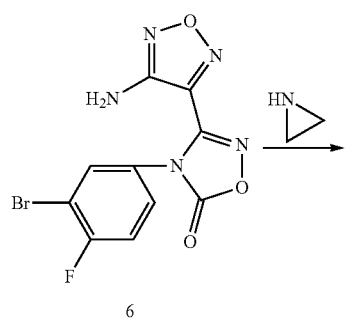

6

According to some embodiments of the present disclosure, in the method disclosed herein, N,N'-carbonyldiimidazole in step (3) may be used at an amount of 1 equivalent to 1.5 equivalents per 1 equivalent by mole of the compound of formula 5. In other embodiments, N,N'-carbonyldiimidazole in step (3) may be used at the amount of 1.11 equivalents per 1 equivalent by mole of the compound of formula 5.

According to some embodiments of the present disclosure, in the step (4) of the method, the compound of formula 6 and acetone are added into the fourth reactor, and the fourth reactor is kept at −10° C.~5° C., then ethyleneimine is added, and the mixture is stirred for 1 hour to 4 hours at −10° C.~5° C. until a lot of solid precipitation formed. The solid is filtered and washed with acetone to obtain the compound of formula 7.

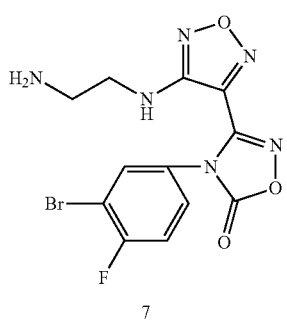

7

According to some embodiments of the present disclosure, in the method disclosed herein, ethyleneimine in the step (4) may be used at an amount of 1 equivalent to 1.3 equivalents per 1 equivalent by mole of compound 6. In other embodiments, ethyleneimine in the step (4) may be used at the amount of 1.05 equivalents per 1 equivalent by mole of compound 6.

According to some embodiments of the present disclosure, in the step (5) of the method, the compound of formula 7, the compound of formula 8 and triethylamine are added into the fifth reactor, then the fifth reactor is heated to 120° C.~140° C. with microwave radiation for 15 minutes to 1 hour. The fifth reactor is cooled down to room temperature, added with ethyl acetate, and the organic phase is washed with queous HCl solution, dehydrated with anhydrous sodium sulfate, filtered and concentrated, the solid is washed with methyl tertiary butyl ether to obtain the compound of formula 9.

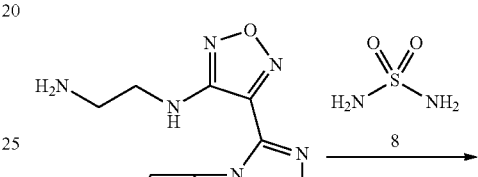

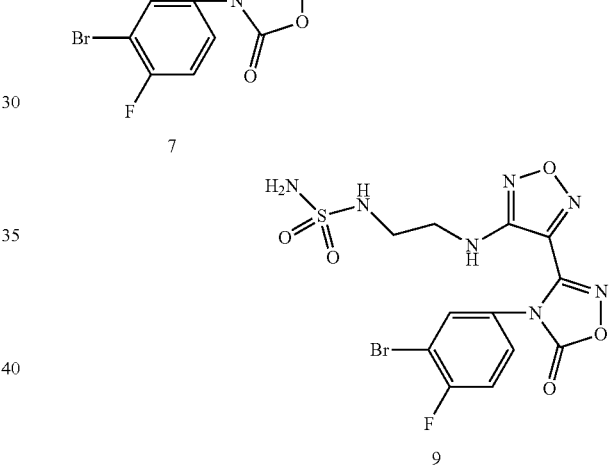

9

According to some embodiments of the present disclosure, in the method disclosed herein, the compound of formula 8 in step (5) may be used at an amount of 1.05 equivalents to 1.5 equivalents per 1 equivalent by mole of the compound of formula 7. In other embodiments, the compound of formula 8 in step (5) may be used at the amount of 1.2 equivalents per 1 equivalent by mole of the compound of formula 7.

According to some embodiments of the present disclosure, in the step (6) of the method, the compound of formula 9 and THF are added into the sixth reactor, the sixth reactor is kept at −10° C.~5° C. while sodium hydroxide solution is added slowly into the sixth reactor, then the mixture is kept at room temperature and stirred for 1 hour to 3 hours. After the reaction, concentrated hydrochloric acid solution is slowly added to the mixture to adjust the pH to 3~4, then add ethyl acetate, the organic phase is washed with water and saturated sodium chloride solution respectively, dried over $Na_2SO_4$, filtered and concentrated to obtain white solid, then the obtained solid was washed with methyl tertiary butyl ether, then filtered and dried to obtain the final product the compound of formula 1 (epacadostat).

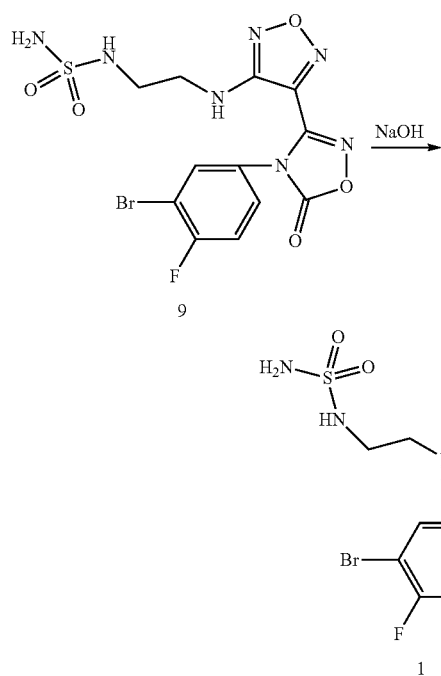

According to some embodiments of the present disclosure, in the method disclosed herein, sodium hydroxide in step (6) may be used at an amount of 3.25 equivalents to 4.18 equivalents per 1 equivalent by mole of the compound of formula 8. In other embodiments, sodium hydroxide in step (6) may be used at the amount of 3.71 equivalents per 1 equivalent by mole of the compound of formula 8.

In the present invention, the term "comprise" is an open expression, it means comprising the contents disclosed herein, but don't exclude other contents.

Compared with the prior art, the advantages of the present invention is as follows:

In the present invention, through adopt the ethyleneimine as reactant, the process is shortened surprisingly, the entire synthetic route has only six steps, and the application of this route is applied to reduce the reaction conditions and improve the yield of the product. And the whole reaction route is simple, economic and easy to control, has high yield, and does not use harsh conditions such as high temperature and high pressure.

EXAMPLES

The new preparation methods of IDO inhibitor epacadostat and intermediates thereof are disclosed in the examples of the present disclosure. Those skilled in the art can learn from this article to properly improve the process parameters to implement the preparation method. It's noted that all the similar replacements and changes are obvious for the skilled person and within the scope of the present disclosure. The methods disclosed herein are described in the preferred examples. Related persons can clearly realize and apply the techniques disclosed herein by making some changes, appropriate alterations or combinations to the methods without departing from spirit, principles and scope of the present disclosure.

In order to further understand the invention, it is detailed below through examples.

Example 1

Preparation of Compound 3

Compound 2 (100 g, 1.52 mol), sodium nitrite (113 g, 1.64 mol) and water (2.3 L) were added into the first reactor, then the first reactor was cooled under 10° C., concentrated hydrochloric acid (8 mL) was added into the first reactor and the temperature was kept below 15° C., then the mixture was kept at room temperature, stirred for 2 hours. Then hydroxylamine hydrochloride (315 g, 4.57 mol) was added, and the mixture was stirred for 1 hour. The mixture was heated to reflux for 2 hours, cooled down to room temperature, NaOH solution was added into the mixture to adjust the pH of the mixture to 7. The first reactor was cooled and then centrifugated to obtain solid precipitation. The wet solid precipitation was dissolved in a mixture of water (1.8 L), acetic acid (1.4 L) and hydrochloric acid (0.74 L) by heating. Sodium nitrite aqueous solution (contain sodium nitrite (96 g, 1.39 mol) and water (250 mL)) was added and the reactor was kept at −10° C.~0° C., and the mixture was stirred for 1 hour to 3 hours, and then the mixture was kept at room temperature. The precipitated reaction product was filtered and dissolved in ethyl acetate (1 L). The organic phase was washed by saturated sodium chloride aqueous solution (200 mL), then dried and concentrated to obtain oily substance. The oily substance was dissolved in methyl tertiary butyl ether (2 L), discolored with active carbon. The solution was filtered and concentrated to give compound 3 (87.6 g, yield 35.6%). MS: 185 [M+Na]$^+$

Example 2

Preparation of Compound 3

Compound 2 (100 g, 1.52 mol), sodium nitrite (113 g, 1.64 mol) and water (2.3 L) were added into the first reactor, then the first reactor was cooled under 10° C., concentrated hydrochloric acid (8 mL) was added into the first reactor and the temperature was kept below 15° C., then the mixture was kept at room temperature, stirred for 3 hours. Then hydroxylamine hydrochloride (295.7 g, 4.256 mol) was added, and the mixture was stirred for 1 hour. The mixture was heated to reflux for 3 hours, cooled down to room temperature, NaOH solution was added into the mixture to adjust the pH of the mixture to 7. The first reactor was cooled down and then centrifugated to obtain solid precipitation. The wet solid precipitation was dissolved in a mixture of water (1.8 L), acetic acid (1.4 L) and hydrochloric acid (0.74 L) by heating. Sodium nitrite aqueous solution (contain sodium nitrite (91.36 g, 1.324 mol) and water (250 mL)) was added and the reactor was kept at −5° C.~5° C., and the mixture was stirred for 1 hour to 3 hours, and then the mixture was kept at room temperature. The precipitated reaction product was filtered and dissolved in ethyl acetate (1 L). The organic phase was washed by saturated sodium chloride aqueous solution (200 mL), then dried and concentrated to obtain oily substance. The oily substance was dissolved in methyl tertiary butyl ether (2 L), discolored with active carbon. The solution was filtered and concentrated to give compound 3 (83.7 g, yield 34.0%).

Example 3

Preparation of Compound 3

Compound 2 (100 g, 1.52 mol), sodium nitrite (113 g, 1.64 mol) and water (2.3 L) were added into the reactor, then the first reactor was cooled under 10° C., concentrated hydrochloric acid (8 mL) was added into the first reactor and the temperature was kept below 15° C., then the mixture was kept at room temperature, stirred for 1 hour. Then hydroxylamine hydrochloride (327.4 g, 4.712 mol) was added, and the mixture was stirred for 1 hour. The mixture was heated to reflux for 1 hour, cooled down to room temperature, NaOH solution was added into the mixture to adjust the pH of the mixture to 7. The first reactor was cooled down and then centrifugated to obtain solid precipitation. The wet solid precipitation was dissolved in a mixture of water (1.8 L), acetic acid (1.4 L) and hydrochloric acid (0.74 L) by heating. Sodium nitrite aqueous solution (contain sodium nitrite (107.1 g, 1.552 mol) and water (250 mL)) was added and the reactor was kept at 0° C.~10° C., and the mixture was stirred for 1 hour to 3 hours, and then the mixture was kept at room temperature. The precipitated reaction product was filtered and dissolved in ethyl acetate (1 L). The organic phase was washed by saturated sodium chloride aqueous solution (200 mL), then dried and concentrated to obtain oily substance. The oily substance was dissolved in methyl tertiary butyl ether (2 L), discolored with active carbon. The solution was filtered and concentrated to give compound 3 (84.9 g, yield 34.5%).

Example 4

Preparation of Compound 5

Compound 3 (80 g, 0.4923 mol), compound 4 (280 g, 1.474 mol) and ethanol (2.4 L) were added into the reactor, then the reactor was heated to reflux for 1 hours, then the mixture was concentrated, and the crude product was washed with n-hexane/ethyl acetate (200 mL, V/V=10:1), filtered, dried to obtain compound 5 (138 g, yield 88.7%).

MS: 316 [M+1]$^+$. $^1$H-NMR (400 Hz, DMSO-d$_6$): □ 11.42 (s, 1H), 8.86 (s, 1H), 7.17 (dd, 1H), 7.08 (dd, 1H), 6.77-6.71 (m, 1H), 6.24 (s, 2H).

Example 5

Preparation of Compound 5

Compound 3 (80 g, 0.4923 mol), compound 4 (187.1 g, 0.9846 mol) and ethanol (2.3 L) were added into the reactor, then the reactor was heated to reflux for 2 hours, then the mixture was concentrated, and the crude product was washed with n-hexane/ethyl acetate (200 mL, V/V=10:1), filtered, dried to obtain compound 5 (131 g, yield 84.2%).

Example 6

Preparation of Compound 5

Compound 3 (80 g, 0.4923 mol), compound 4 (280 g, 1.723 mol) and ethanol (2.5 L) were added into the reactor, then the reactor was heated to reflux for 30 minutes, then the mixture was concentrated, and the crude product was washed with n-hexane/ethyl acetate (200 mL, V/V=10:1), filtered, dried to obtain compound 5 (135 g, yield 86.8%).

Example 7

Preparation of Compound 6

Compound 5 (200 g, 0.6327 mol) and ethyl acetate (2 L) were added into the reactor, then N,N'-carbonyldiimidazole (113.4 g, 0.6994 mol) was added into the reactor at room temperature. The reactor was heated to 63° C.-68° C., then the mixture was stirred for 2 hours, cooled down to room temperature, the mixture was concentrated, the solid residue was washed with n-hexane to obtain compound 6 (207.6 g, yield 95.9%).

Ms: 342 [M+1]$^+$, $^1$H-NMR (400 Hz, DMSO-d$_6$): □□ 8.06 (d, 1H), 7.72-7.66 (m, 1H), 7.58 (d, 1H), 6.60 (s, 2H).

Example 8

Preparation of Compound 6

Compound 5 (200 g, 0.6327 mol) and ethyl acetate (2 L) were added into the reactor, then N,N'-carbonyldiimidazole (102.6 g, 0.6327 mol) was added into the reactor at room temperature. The reactor was heated to 60° C.-65° C., then the mixture was stirred for 3 hours, cooled down to room temperature, the mixture was concentrated, the solid residue was washed with n-hexane to obtain compound 6 (197.0 g, yield 91.0%/).

Example 9

Preparation of Compound 6

Compound 5 (200 g, 0.6327 mol) and ethyl acetate (2.2 L) were added into the reactor, then N,N'-carbonyldiimidazole (153.9 g, 0.9491 mol) was added into the reactor at room temperature. The reactor was heated to 65° C.-70° C., then the mixture was stirred for 1 hour, cooled down to room temperature, the mixture was concentrated, the solid residue was washed with n-hexane to obtain compound 6 (202.4 g, yield 93.5%).

Example 10

Preparation of compound 7

Compound 6 (80 g, 0.2338 mol) and acetone (500 mL) were added into the fourth reactor, and the reactor was kept at −5° C.~0° C., then ethyleneimine (10.1 g, 0.2345 mol) was added into the reactor, and the mixture was stirred for 1 hour to 4 hours at −5° C.~0° C. until a lot of solid precipitation formed. The solid was filtered and washed with acetone to obtain compound 7 (85.3 g, yield 94.7%).

Ms: 385 [M+1]$^+$, $^1$H-NMR (400 Hz, DMSO-d$_6$): □□ 8.06 (d, 1H), 7.72-7.66 (m, 1H), 7.58 (d, 1H), 4.5 (s, 1H), 3.36 (dd, 2H), 3.08 (dd, 2H).

Example 11

Preparation of Compound 7

Compound 6 (80 g, 0.2338 mol) and acetone (500 mL) were added into the fourth reactor, and the reactor was kept at −10° C.~−5° C., then added ethyleneimine (13.1 g, 0.3039 mol) was added into the reactor, and the mixture was stirred for 1 hour to 4 hours at −10° C.~−5° C. until a lot of solid precipitation formed. The solid was filtered and washed with acetone to obtain compound 7 (83.9 g, yield 93.1%).

Example 12

Preparation of Compound 7

Compound 6 (80 g, 0.2338 mol) and acetone (500 mL) were added into the fourth reactor, and the reactor was kept at 0° C.~5° C., then ethyleneimine (10.6 g, 0.2455 mol) was added into the reactor, and the mixture was stirred for 1 hour to 4 hours at 0° C.~5° C. until a lot of solid precipitation formed. The solid was filtered and washed with acetone to obtain compound 7 (85.6 g, yield 95.0%).

Example 13

Preparation of compound 9

Compound 7 (100 g, 0.2596 mol), compound 8 (30 g, 0.3121 mol) and triethylamine (400 mL) was added into the fifth reactor, then the reactor was heated to 130° C. with microwave radiation for 30 minutes. The reactor was cooled down to room temperature, added ethyl acetate (1000 mL) was added into the reactor, and the organic phase of the resulting mixture was washed with 1N aqueous HCl solution (200 mL), dehydrated with anhydrous sodium sulfate, filtered and concentrated, the solid was washed with methyl tertiary butyl ether to obtain compound 9 (109.7 g, yield 91.0%).

MS: 464 [M+H]$^+$, $^1$H-NMR (400 Hz, DMSO-d$_6$): δ 8.08 (dd, 1H), 7.72 (m, 1H), 7.59 (t, 1H), 6.67 (t, 1H), 6.52 (t, 1H), 3.38 (dd, 2H), 3.11 (dd, 6.3 Hz).

Example 14

Preparation of Compound 9

Compound 7 (100 g, 0.2596 mol), compound 8 (26.2 g, 0.2726 mol) and triethylamine (400 mL) were added into the fifth reactor, then the reactor was heated to 120° C. with microwave radiation for 1 hour. The reactor was cooled down to room temperature, ethyl acetate (1000 mL) was added into the reactor, and the organic phase of the resulting mixture was washed with 1N queous HCl solution (180 mL), dehydrated with anhydrous sodium sulfate, filtered and concentrated, the solid was washed with methyl tertiary butyl ether to obtain compound 9 (106.6 g, yield 88.4%).

Example 15

Preparation of Compound 9

Compound 7 (100 g, 0.2596 mol), compound 8 (37.4 g, 0.3894 mol) and triethylamine (400 mL) were added into the fifth reactor, then the reactor was heated to 140° C. with microwave radiation for 15 minutes. The reactor was cooled down to room temperature, ethyl acetate (1000 mL) was added into the reactor, and the organic phase of the resulting mixture was washed with 1N queous HCl solution (220 mL), dehydrated with anhydrous sodium sulfate, filtered and concentrated, the solid was washed with methyl tertiary butyl ether to obtain compound 9 (107.4 g, yield 89.1%).

Example 16

Preparation of Epacadostat

Compound 9 (10 g, 0.02154 mol) and THF (50 mL) were added into the sixth reactor, the reactor was kept at −10° C.~−5° C. while 2N sodium hydroxide solution (40 mL) was added slowly into it, then the mixture was kept at room temperature and stirred for 3 hours. After the reaction, concentrated hydrochloric acid solution was slowly added to the mixture to adjust the pH to 3~4, then add ethyl acetate (500 mL) was added into the resulting mixture, the organic phase was washed with water (150 mL) and saturated sodium chloride solution (150 mL) respectively, dried over Na$_2$SO$_4$, filtered and concentrated to obtain white solid, then the obtained solid was washed with methyl tertiary butyl ether (50 mL), then filtered and dried to obtain the final product compound 1 (epacadostat, 8.34 g, yield 88.5%), HPLC purity: 99.6%.

Ms: 460[M+Na]$^+$, $^1$H-NMR (400 Hz, DMSO-d6): δ 11.51 (s, 1H), 8.90 (s, 1H), 7.17 (t, 1H), 7.11 (dd, 1H), 6.76 (t, 1H), 6.59 (s, 2H), 6.23 (t, 1H), 3.35 (d, 2H), 3.10 (dd, 2H).

Example 17

Preparation of Epacadostat

Compound 9 (10 g, 0.02154 mol) and THF (50 mL) were added into the sixth reactor, the reactor was kept at −5° C.~0° C. while 2N sodium hydroxide solution (35 mL) was added slowly into it, then the mixture was kept at room temperature and stirred for 2 hours. After the reaction, concentrated hydrochloric acid solution was slowly added to the mixture to adjust the pH to 3~4, then add ethyl acetate (500 mL) was added into the resulting mixture, the organic phase was washed with water (150 mL) and saturated sodium chloride solution (150 mL) respectively, dried over Na$_2$SO$_4$, filtered and concentrated to obtain white solid, then the obtained solid was washed with methyl tertiary butyl ether (50 mL), then filtered and dried to obtain the final product of compound 1 (epacadostat, 8.21 g, yield 87.0%), HPLC purity: 99.4%.

Example 18

Preparation of Epacadostat

Compound 9 (10 g, 0.02154 mol) and THF (50 mL) were added into the sixth reactor, the reactor was kept at 0° C.~5° C. while 2N sodium hydroxide solution (45 mL) was added slowly into it, then the mixture was kept at room temperature and stirred for 1 hour. After the reaction, concentrated hydrochloric acid solution was slowly added to the mixture to adjust the pH to 3~4, then ethyl acetate (500 mL) was added into the resulting mixture, the organic phase was washed with water (150 mL) and saturated sodium chloride solution (150 mL) respectively, dried over Na$_2$SO$_4$, filtered and concentrated to obtain white solid, then the obtained solid was washed with methyl tertiary butyl ether (50 mL), then filtered and dried to obtain the final product of compound 1 (epacadostat, 8.29 g, yield 87.8%), HPLC purity: 99.5%.

In the specification, unless specified or limited otherwise, terms such as "first" and "second" are used herein for purposes of description and are not intended to indicate or imply relative importance or significance.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for preparing epacadostat of formula 1, comprising:
   (1) contacting a compound of formula 2 with sodium nitrite and hydroxylamine hydrochloride to obtain a compound of formula 3;
   (2) contacting the compound of formula 3 with a compound of formula 4 to obtain a compound of formula 5;
   (3) contacting the compound of formula 5 with N,N'-carbonyldiimidazole to obtain a compound of formula 6;
   (4) contacting the compound of formula 6 with ethyleneimine to obtain a compound of formula 7;
   (5) contacting the compound of formula 7 with a compound of formula 8 to obtain a compound of formula 9; and
   (6) contacting the compound of formula 9 with sodium hydroxide to obtain the epacadostat of formula 1;

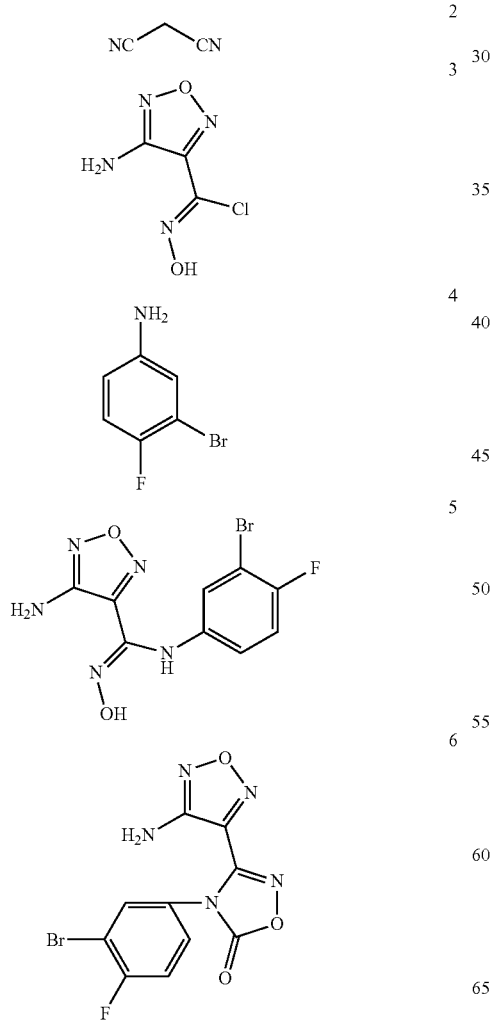
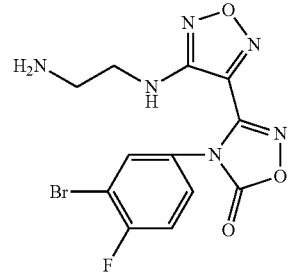
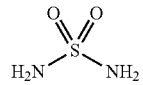
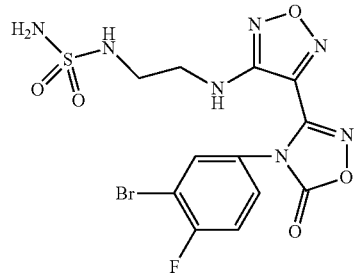
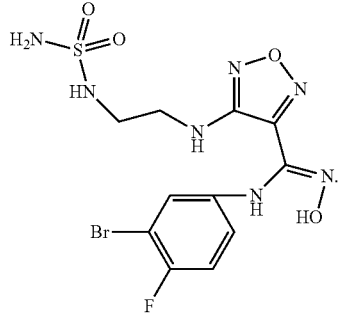

2. The method of claim 1, wherein the step (1) comprises:
   (1-1) dissolving the compound of formula 2 and sodium nitrite in water under about 10° C., adding concentrated hydrochloric acid into the resulting mixture under a temperature below 15° C. to obtain a first mixture, and stirring the first mixture at room temperature for about 1 hour to about 3 hours;
   (1-2) adding hydroxylamine hydrochloride into the first mixture to obtain a second mixture, and stirring the second mixture for about 1 hour;
   (1-3) heating the second mixture at refluxing temperature for about 1 hour to about 3 hours, then cooling down the temperature of the second mixture to room temperature, then adjusting pH of the second mixture to about 7 by adding NaOH solution;
   (1-4) centrifugating the resulting reaction product of the step (1-3) to obtain a first precipitation;
   (1-5) dissolving the first precipitation in a mixture of water, acetic acid and hydrochloric acid by heating, and adding sodium nitrite aqueous solution into the resulting mixture under a temperature ranging from about −10° C. to about 10° C. to obtain a third mixture, and stirring the third mixture for about 1 hour to about 3 hours at room temperature to obtain a second precipitation;

(1-6) dissolving the second precipitation in ethyl acetate to obtain a fourth mixture;
(1-7) obtaining an oily substance by drying and concentrating the organic phase of the fourth mixture;
(1-8) dissolving the oily substance in methyl tertiary butyl ether to obtain a fifth mixture, and discoloring the fifth mixture with active carbon;
(1-9) concentrating the resulting reaction product of the step (1-8) to obtain the compound of formula 3.

3. The method of claim 2, wherein a molar ratio between the compound of formula 2, sodium nitrite and hydroxylamine hydrochloride is 1:(1.95-2.1):(2.8-3.1).

4. The method of claim 3, wherein the molar ratio between the compound of formula 2, sodium nitrite and hydroxylamine hydrochloride is 1:1.99:3.

5. The method of claim 1, wherein the compound of formula 3 is contacted with the compound of formula 4 in ethanol under a condition of refluxing.

6. The method of claim 5, wherein the amount of the compound of formula 4 is 2 equivalents to 3.5 equivalents per 1 equivalent by mole of the compound of formula 3.

7. The method of claim 6, wherein the amount of the compound of formula 4 is 2.99 equivalents per 1 equivalent by mole of the compound of formula 3.

8. The method of claim 1, wherein the compound of formula 5 is contacted with N,N'-carbonyldiimidazole in ethyl acetate under a temperature ranging from about 60° C. to about 70° C. for about 1 hour to about 3 hours.

9. The method of claim 8, wherein the amount of N,N'-carbonyldiimidazole is 1 equivalent to 1.5 equivalents per 1 equivalent by mole of the compound of formula 5.

10. The method of claim 9, wherein the amount of N,N'-carbonyldiimidazole is 1.11 equivalent per 1 equivalent by mole of the compound of formula 5.

11. The method of claim 1, wherein the compound 6 is contacted with ethyleneimine in acetone under a temperature ranging from about −10° C. to about 5° C. for about 1 hour to 4 hours.

12. The method of claim 11, wherein the amount of ethyleneimine is 1 equivalent to 1.3 equivalents per 1 equivalent by mole of the compound of formula 6.

13. The method of claim 12, wherein the amount of ethyleneimine is 1.05 equivalents per 1 equivalent by mole of the compound of formula 6.

14. The method of claim 1, wherein the step (5) comprises:
(5-1) contacting the compound of formula 7 with the compound of formula 8 in triethylamine under a temperature ranging from about 120° C. to about 140° C. with microwave radiation for about 15 minutes to about 1 hour to obtain a sixth mixture;
(5-2) cooling down the temperature of the sixth mixture to room temperature, and adding ethyl acetate into the sixth mixture to obtain an seventh mixture;
(5-3) washing the organic phase of the seventh mixture with aqueous HCl solution, dehydrating the organic phase of the seventh mixture with anhydrous sodium sulfate, then concentrating the organic phase of the seventh resulting mixture to obtain the compound of formula 9.

15. The method of claim 14, wherein the amount of the compound of formula 8 is 1.05 equivalents to 1.5 equivalents per 1 equivalent by mole of the compound of formula 7.

16. The method of claim 15, wherein the amount of the compound of formula 8 is 1.2 equivalents per 1 equivalent by mole of the compound of formula 7.

17. The method of claim 1, wherein the step (6) comprise:
(6-1) dissolving the compound 9 in THF under a temperature ranging from about −10° C. to about 5° C.;
(6-2) adding sodium hydroxide solution into the solution obtained by the step (6-1) at room temperature to obtain an eighth mixture, and stirring the eighth mixture for 2 hours;
(6-3) adjusting the pH of the eighth mixture of the step (6-2) to about 3 to about 4 by adding hydrochloric acid solution, and adding ethyl acetate in to the eighth mixture to obtain a ninth resulting mixture;
(6-4) washing the ninth mixture with water and saturated sodium chloride solution respectively, and concentrating the ninth mixture to obtain epacadostat of formula 1.

18. The method of claim 17, wherein the amount of sodium hydroxide is 3.25 equivalents to 4.18 equivalents per 1 equivalent by mole of the compound of formula 9.

19. The method of claim 18, wherein the amount of sodium hydroxide is 3.71 equivalents per 1 equivalent by mole of the compound of formula 9.

* * * * *